(12) United States Patent
Massaro

(10) Patent No.: US 7,278,328 B2
(45) Date of Patent: Oct. 9, 2007

(54) METHOD AND APPARATUS FOR HANDLING SAMPLE HOLDERS

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 398 days.

(21) Appl. No.: 10/934,342

(22) Filed: Sep. 3, 2004

(65) Prior Publication Data

US 2006/0051239 A1    Mar. 9, 2006

(51) Int. Cl.
*G01N 1/22*    (2006.01)

(52) U.S. Cl. ................. 73/863.01; 73/864.91

(58) Field of Classification Search .......... 73/863, 73/863.31, 864.21, 864.81, 864.91, 863.01; 436/43, 47; 422/62, 63, 65, 68.1
See application file for complete search history.

(56) References Cited

U.S. PATENT DOCUMENTS

| | | | | |
|---|---|---|---|---|
| 4,266,674 A | * | 5/1981 | Bell et al. | 209/536 |
| 4,751,184 A | | 6/1988 | Higo et al. | 422/65 |
| 5,551,828 A | * | 9/1996 | Iles | 414/757 |
| 5,663,545 A | * | 9/1997 | Marquiss | 235/375 |
| 5,869,006 A | * | 2/1999 | Fanning et al. | 422/67 |
| 5,885,530 A | * | 3/1999 | Babson et al. | 422/65 |
| 6,085,603 A | | 7/2000 | Rickkinen | 73/864.21 |
| 6,141,602 A | * | 10/2000 | Igarashi et al. | 700/226 |
| 6,465,770 B2 | * | 10/2002 | Gseller | 250/221 |
| 6,598,796 B2 | * | 7/2003 | Harrop | 235/462.01 |
| 6,832,722 B1 | * | 12/2004 | Cocola et al. | 235/385 |
| 2002/0017602 A1 | * | 2/2002 | Gseller | 250/221 |
| 2004/0014228 A1 | | 1/2004 | Brignac, Jr. et al. | 436/43 |
| 2005/0036907 A1 | * | 2/2005 | Shoji | 422/58 |

FOREIGN PATENT DOCUMENTS

| | | |
|---|---|---|
| AT | 399050 B | 1/2004 |
| EP | 0183097 A1 | 6/1986 |
| EP | 258565 A2 * | 3/1988 |
| GB | 2120786 A | 12/1983 |
| WO | WO9930824 A | 6/1999 |

* cited by examiner

Primary Examiner—Hezron Williams
Assistant Examiner—Tamiko Bellamy
(74) Attorney, Agent, or Firm—Wolf, Greenfield & Sacks, P.C.

(57) ABSTRACT

A sample handling apparatus identifies sample holders and their location in a sample holder carrier. This information may be used to determine the identity of sample holders based only on location in the carrier during subsequent processing of material contained in the sample holders. Sample holder identity may be automatically read, and placement of holders in a carrier may be automatically determined and correlated with the holder identity. Such information may be stored, e.g., in a memory in the carrier so that sample holders can be easily identified later.

21 Claims, 4 Drawing Sheets

METHOD AND APPARATUS FOR HANDLING SAMPLE HOLDERS

FIELD OF INVENTION

This invention relates to handling sample holders. More particularly, this invention relates to automated identification and tracking of unique sample holders in a processing apparatus.

BACKGROUND OF INVENTION

Sample processing apparatus are widely used, for example, in performing diagnostic tests on blood samples or other materials contained in individual sample holders. When using these processing apparatus, individual sample holders, e.g., in the form of individual tubes, are provided to the processing apparatus, which removes one or more portions of the material in one or more sample holders and performs various operations using the material, such as genomic or other analytic tests.

SUMMARY OF INVENTION

The inventor(s) has(have) appreciated that significant delays can occur with existing processing apparatus as a result of failed or inaccurate identification of sample holders during processing. That is, processing apparatus typically identify each sample holder immediately before withdrawing material from the holder, such as by reading a barcode on the sample holder. By identifying each sample holder, the processing apparatus can associate test results with the sample holder from which the tested material was removed (and as a result, associate the test results with the correct person or other source of the sample material). In some cases, identification of the sample holder fails, e.g., because a barcode on the holder is improperly read or not read. This causes the apparatus to stop processing so that the reading error can be corrected.

In one aspect of the invention, a method and apparatus are provided to help ensure the proper identification of sample holders in a processing apparatus, thereby potentially preventing delays associated with misidentified or non-identified sample holders. In one illustrative embodiment, individual sample holders, e.g., test tube-like vials, are scanned to read a barcode or other unique identifier on the sample holders before the holders are loaded in to a multi-location carrier. Reading of the barcode or other unique identifier can be performed by a machine reading device (e.g., a barcode scanner) as a robotic manipulator or operator holds the sample holder near the machine reading device. After proper reading, the sample holder may be placed in the carrier and its location in the carrier detected so that the identity of each holder in each position in the carrier is known. Thus, when sample holders are later accessed in the carrier to remove material for analysis, the identity of the sample holder may be known based on its location in the carrier, and individual sample holders need not have a barcode or other identifier read immediately before material is withdrawn.

In one aspect of the invention, a sample handling apparatus for use with a processing apparatus that performs analytical processes on material in a plurality of sample holders includes a reading apparatus that inputs information representing a machine readable identifier on individual sample holders each containing a material to be used in analytical processes. At least one carrier is constructed and arranged to hold a plurality of individual sample holders at a plurality of unique locations, and a control system receives a signal from the reading apparatus corresponding to an identifier from an individual sample holder. The identifier information is correlated with the location of the corresponding sample holder in the carrier so that results from analytical processes performed on sample material removed from the sample holder can be properly correlated with the sample holder.

In one aspect, the apparatus includes a detector that detects the presence or absence of a sample holder in each location in a carrier. Thus, the control system may correlate an identity of each sample holder with its location in a carrier by associating a machine readable identifier read by the reading apparatus with a subsequent detection of the sample holder in a particular location in the carrier.

In another aspect of the invention, a method for performing processes on material carried in sample holders includes providing a plurality of sample holders with each sample holder carrying material. An identifier on each of the sample holders is read, e.g., machine read, and each of the sample holders is placed in a corresponding location in a carrier. Information regarding the correlation of the identifier read from each sample holder and the location of the sample holder in the carrier is stored, and the carrier and sample holders are provided to a processing apparatus for performing analytical processes on the material in the sample holders.

These and other aspects of the invention will be apparent and/or obvious from the following description of illustrative embodiments and the appended claims.

BRIEF DESCRIPTION OF DRAWINGS

Aspects of the invention will be more clearly appreciated from the following detailed description, when taken in conjunction with the accompanying drawings, wherein like numbers are used for like features, in which.

DETAILED DESCRIPTION

Various aspects of the invention are described below with reference to illustrative embodiments. However, it should be understood that aspects of the invention are not limited to those embodiments described below, but instead may be used in any suitable system or arrangement.

Figure 1:
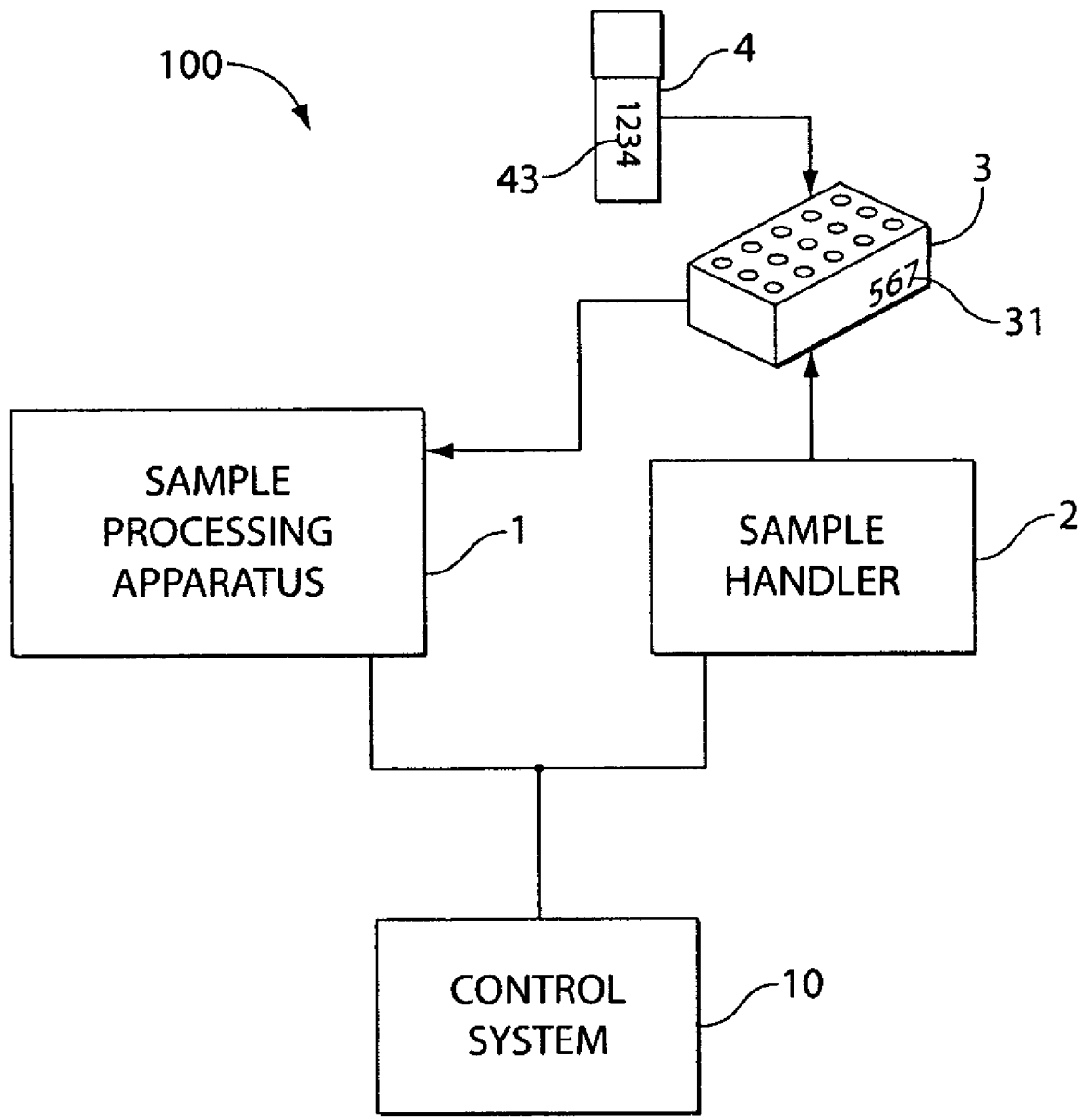
FIG. 1 is a schematic diagram of a sample handling and processing apparatus according to the invention.

FIG. 1 shows a schematic block diagram of a sample handling and processing arrangement 100 according to one aspect of the invention. In this illustrative embodiment, a sample processing apparatus 1 may perform any one of several different processes on sample materials. For example, the sample processing apparatus 1 may perform one or more analytic tests on one or more blood or other material samples. The blood or other material may be provided to the processing apparatus 1 in one or more vials or other sample holders 4 arranged in one or more racks or carriers 3 that each support a plurality of holders 4. The processing apparatus 1 may then remove all or a part of the material carried in one or more of the holders 4, and subject the material to one or more processes, as is known in the art.

Such analytic processes may include blood typing, genomic fragment separation, chemical or pathogen detection, etc., as the specific analytic processes performed are not necessarily important to aspects of the invention.

In accordance with one aspect of the invention, a sample handler 2 may be provided to help organize sample holders 4 in carriers 3, and/or to individually identify each sample holder 4 and its location in one of a plurality of carriers 3. For example, an identifier 43 on each sample holder 4 may be detected by the sample handler 2 and control system 10 along with the specific location of the holder 4 in a particular carrier 3. In addition, each carrier may include an identifier 31 that is detected by the sample handler 2 and control system 10. Thus, the control system 10 may receive and store information regarding the identity of each sample holder, the location of the sample holder in a carrier, and the identity of the carrier in which the holder is located, i.e., receive and store holder identity/location/carrier information for all holders. Such information may be used by the control system 10 (which together with the sample handler 2 may form a sample handling apparatus) to associate results from analytic tests or other procedures by the processing apparatus 1 with particular sample holders 4, and therefore to a source or sources of the material carried by the sample holders 4.

As a result, the processing apparatus 1 may perform its processes on material withdrawn from sample holders 4 in carriers 3 while only keeping track of the carrier 3 and particular location in the carrier 3 from which material is withdrawn. Results from the processing of the material samples by the processing apparatus 1 may later be correlated to a particular sample holder without requiring the processing apparatus 1 to detect the identity each sample holder 4. That is, the processing apparatus 1 need only keep track of the carrier and the location of the holder in the carrier from which the material was withdrawn. This information is suitable to correlate the results with a particular sample holder 4 since the control system 10 can store information regarding which sample holder 4 was positioned in each location in each carrier 3 provided to the processing apparatus 1. Alternately, the control system 10 may provide the sample holder identity/location/carrier information to the processing apparatus 1, which may use the information to correlate the identity of a sample holder 4 to material withdrawn from it and results of processes performed on the material. In another illustrative embodiment, holder identity/location/carrier information along with other information, such as the particulars of a person from which material was taken for each holder, may be stored in a data processing device incorporated into the carrier 3. With this arrangement, the processing apparatus 1 may communicate with the carrier 3 either by wire or wirelessly to receive identity/location/carrier information and/or other information as needed.

One potential advantage of this aspect of the invention is that the processing apparatus 1 need not directly determine the identity of a sample holder 4 at the time of withdrawing material from the holder 4, e.g., by reading an identifier on the holder 4. As discussed above, determining the identity of each sample holder 4 in this fashion can cause delays in system operation, e.g., caused by requiring a sample holder identifier reading step and/or errors in such reading. Instead, the identity of sample holders in specific carrier locations is determined before material is withdrawn and the processing apparatus 1 need only keep track of the carrier and location in the carrier from which material is withdrawn.

The sample handler 2 and/or control system 10 may be physically incorporated with the sample processing apparatus 1, may be a stand-alone system, or may be part of another processing apparatus. For example, if the sample handling apparatus is incorporated into a processing apparatus, an operator may load individual sample holders 4 into a carrier 3 that is loaded into the processing apparatus 1, reading each identifier on each holder 4 before placing the holder 4 in its place in the carrier 3. Once loading is complete, the processing apparatus 1 may begin processing material in the carrier. Alternately, if the sample handling apparatus is part of another processing apparatus, the holders 4 and carriers 3 may be transferred from one processing apparatus to another processing apparatus along with identity/location/carrier information as needed. Holder identity/location/carrier information may be transferred from one processing apparatus to another to allow for sample holder identification by the subsequent processing apparatus. In a stand-alone arrangement, the sample holder 2 may allow for reading and loading of sample holders 4 into carriers 3 while determining the holder identity/location/carrier information for each holder 4. Other information may be received and stored, such as particulars of a person or other source of the material in one or more holders. Completed carriers 3 may then be provided to a processing apparatus or for other operations along with the sample holder identity/location/carrier information as needed.

The control system 10 may be physically incorporated with the sample handler 2 or may be physically separate therefrom, although in either case still forming a sample handling apparatus with the sample handler 2. In addition, the control system 10 may receive and/or send signals from/to the sample handler 2, the processing apparatus 1 and/or other devices in any suitable way, such as by wired and/or wireless link, by shared network or dedicated link, and/or in any suitable format and/or communications protocol. The control system 10 and/or sample handler 2 may include any suitable general purpose data processing system, which can be, or include, a suitably programmed general purpose computer, or network of general purpose computers, and other associated devices, including communication devices, and/or other circuitry or components necessary to perform the desired input/output or other functions. The control system 10 can also be implemented at least in part as single special purpose integrated circuits (e.g., ASICs), or an array of ASICs, each having a main or central processor section for overall, system-level control and separate sections dedicated to performing various different specific computations, functions and other processes under the control of the central processor section. The control system 10 can also be implemented using a plurality of separate dedicated programmable integrated or other electronic circuits or devices, e.g., hardwired electronic or logic circuits, such as discrete element circuits or programmable logic devices. The control system 10 and/or sample handler 2 may also include other devices, such as an information display device, user input devices, such as a keyboard, user pointing device, touch screen or other user interface, data storage devices, communication devices or other electronic circuitry or components.

Figure 2:
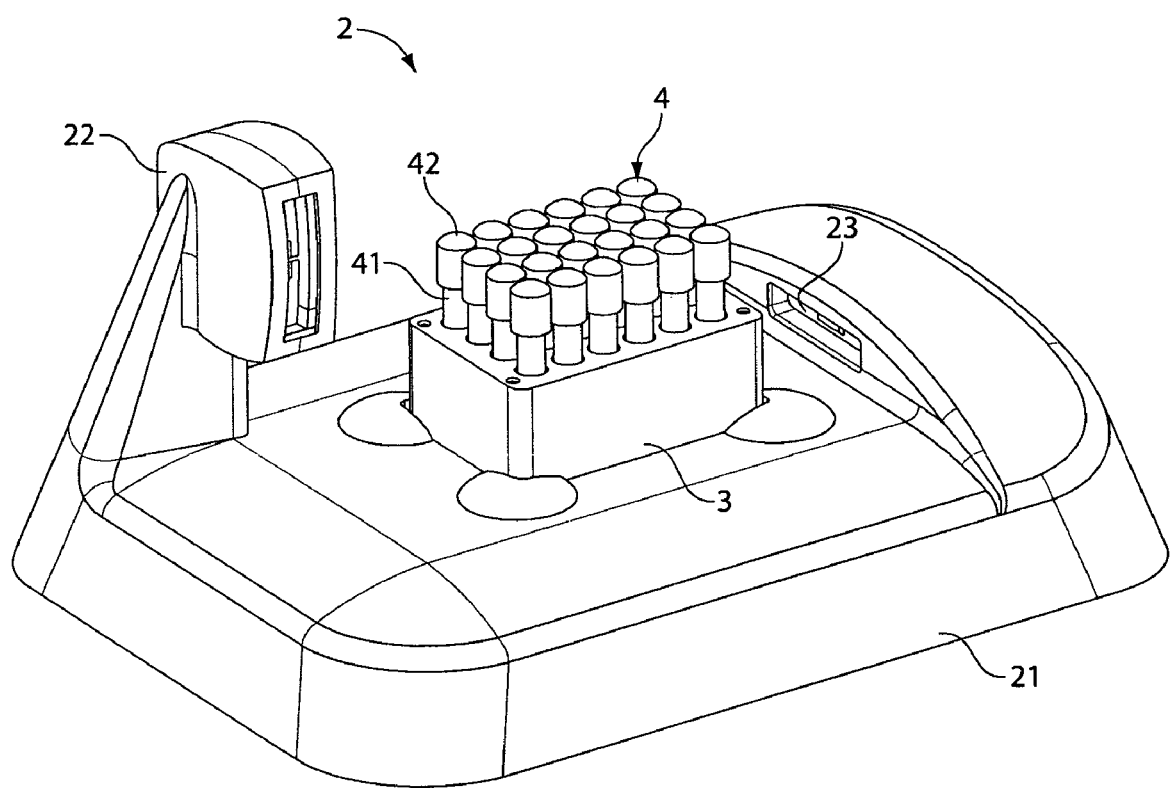
FIG. 2 is a left side perspective view of a sample handling apparatus according to the invention.
Figure 3:
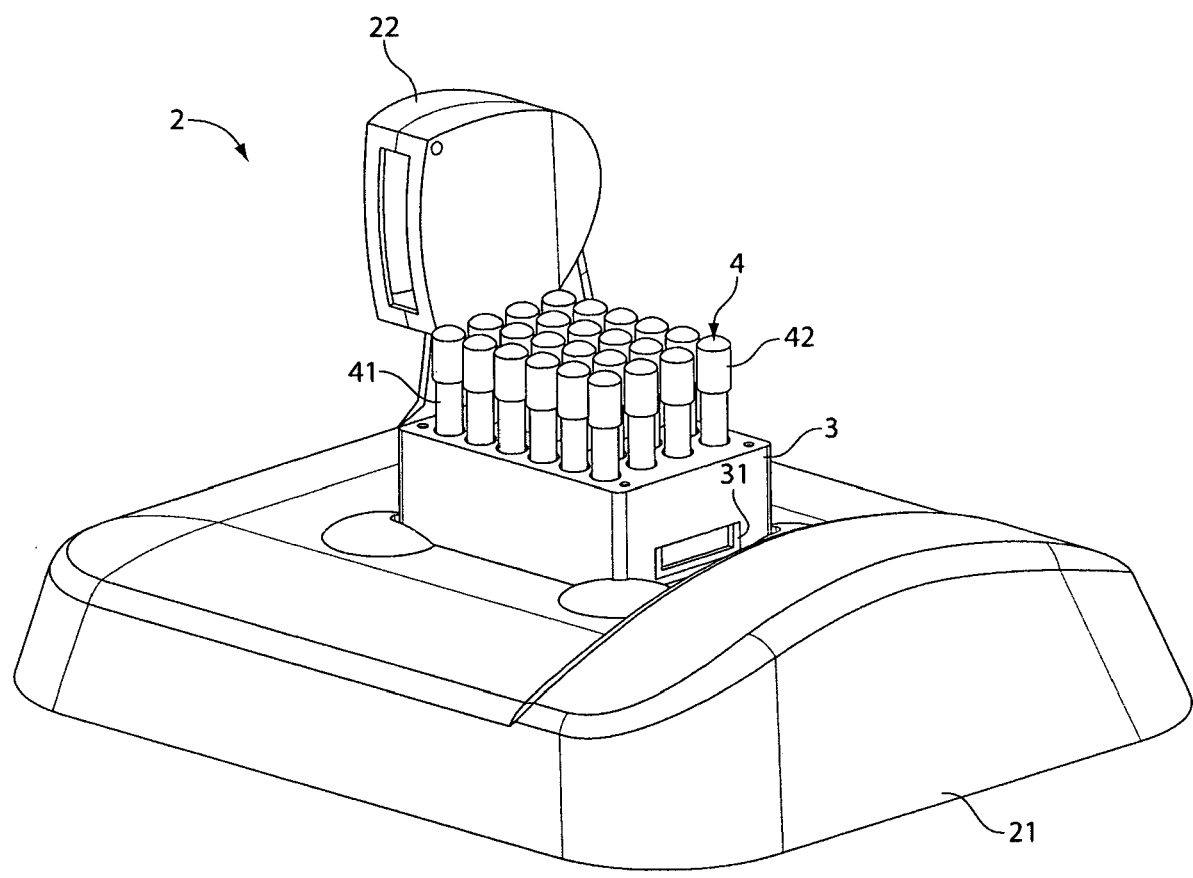
FIG. 3 is a right side perspective view of the FIG. 2 sample handling apparatus.
Figure 4:
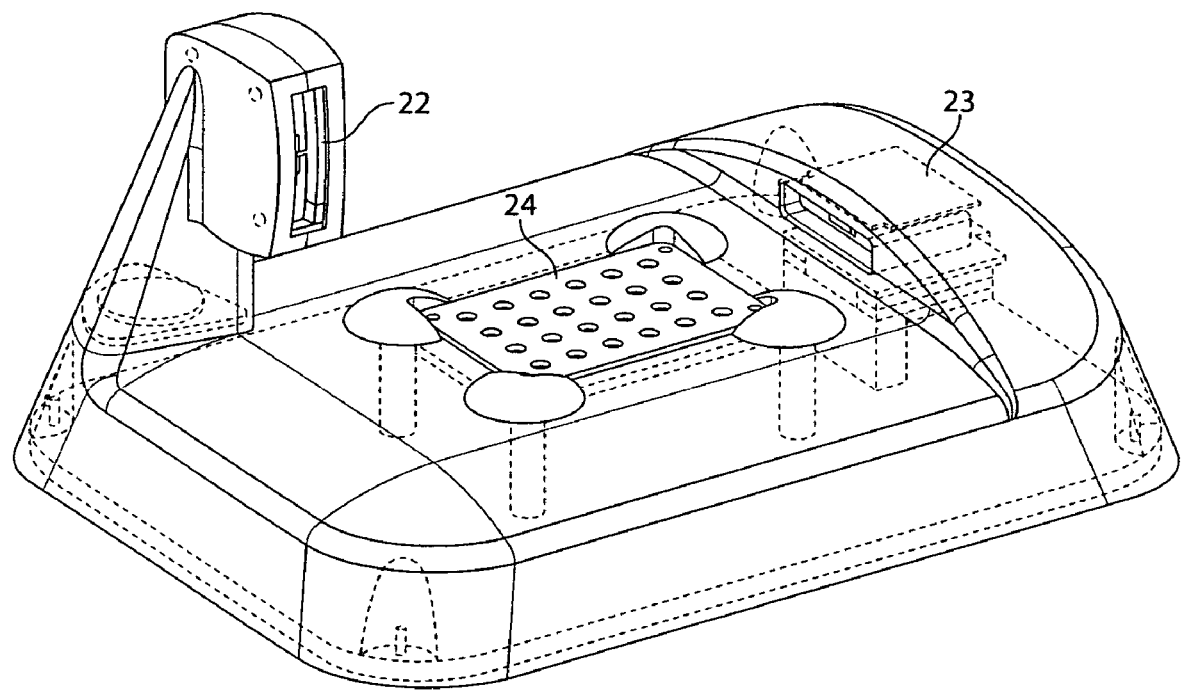
FIG. 4 is a phantom perspective view of the FIG. 2 sample handling apparatus.

FIGS. 2-4 show one embodiment of a sample handler in accordance with one aspect of the invention. In this illustrative embodiment, the sample handler 2 includes a base 21 on which a carrier 3 may be placed, although the sample handler 2 may be arranged to accommodate two or more carriers 3 simultaneously. In this embodiment, the carriers 3 accommodate 24 sample holders 4 that each have a tubular vial 41 and cap 42. It should be understood, however, that the carriers 3 may accommodate different numbers of sample holders 4, and/or that the sample holders 4 may have shapes, sizes or configurations other than cylindrical tube-like structures. The sample handler 2 may include a reader 22 that is capable of inputting, e.g., reading, information regarding an identifier 43 on each sample holder 4. The identifier 43 may uniquely identify one or more sample holders 4 from one or more other sample holders 4 (or not), and may take the form of a machine readable item, such as a barcode, alphanumeric text, radio frequency tag (passive or active), color code, encoded magnetic strip, biometric information (such as a fingerprint or iris pattern), a programmable data processor (microchip) with memory, etc. More than one identifier 43 may be provided for each holder 4, e.g., to provide redundancy and/or increased information content in reading operations. Consequently, the reader 2 may take any suitable arrangement capable of inputting the identifier information from holders 4, typically depending on the form of the identifier(s) used on holders 4, e.g., include a barcode reader, a tag reader, magnetic strip reader, circuitry suitable for wired or wireless communications with a programmable data processor, etc.

The sample handler 2 may also include a carrier reader 23 that inputs information regarding one or more identifiers 31 (FIG. 3) on a carrier 3 placed on the base 21. As with the sample holders 4, any suitable identifier may be used, and the carrier reader 23 may include any suitable device(s) for reading the identifier(s) 31. Thus, for example, the carrier 3 may include an identifier 31 in the form of a programmable data processor having a memory that stores holder identity/location/carrier information and/or other information, such as processing details for specific holders in the carrier, particulars regarding the source of material in the holders, or other. The processing apparatus 1 or other device may read this information from the carrier 3 for correlating test results, performing specific analytic functions on material, etc. Further, the reader 22 could be adapted to read both carrier identifiers 31 and holder identifiers 43 rather than having two readers. Rather than having the readers machine read information from identifiers, the reader 22 or 23 may include a user input device (touch screen and graphical user interface, keyboard, mouse, voice recognition system, etc.) by which an operator can provide identifier information regarding the holders 4 and/or carriers 3 to the sample handler 2. Thus, for example, an operator could view and input identifier information on a holder 4 or carrier 3 (e.g., alphanumeric text) by typing or speaking the identifier information to the reader 22 or 23.

The sample handler 2 may also include a marking device (such as a printer, magnetic strip encoder, transceiver device for electronically communicating with/programming a data processor associated with a holder or carrier, etc.) that marks a holder and/or carrier identifier with desired information. (As used herein, "marking" includes physical alteration with human visible or invisible information, such as printing a barcode or alphanumeric text, as well as programming or other information change in a data processor or other electronic device, etc.) With such an arrangement, holders 4 may be given identifier information as they are loaded into carriers 3 or at another suitable time. For example, a holder 4 may be given identifier information by the control system 10, which instructs the marking device to print, encode or otherwise provide the information to the holder 4. The newly marked holder 4 may then have the identifier 43 read by the reader 22 and then be placed in the carrier 3, or simply be placed in the carrier 3 without reading of the identifier 43.

As shown in FIG. 4, the handling device 2 may include a detector 24 that detects the presence/absence of holders in a carrier 3. In this embodiment, the detector 24 includes individual photosensors adjacent each holder location in the carrier 3 so that each of the photosensors can detect whether a holder is placed in a corresponding location in the carrier 3 or not. It should be understood that the detector 24 may include any suitable devices for detecting holders and operate in any suitable way. For example, the detector 24 may include a video camera and video processing software that analyzes a video image(s) to detect the placement of a holder 4 in one or more locations in the carrier 3. The detector 24 may alternately include electronic switches that change state by the presence/absence of a holder 4 in a corresponding location in a carrier 3. The switches may be built into the carrier 3, e.g., a plurality of switch arms that each extend into a corresponding holder location and are moved when the holder is placed in/removed from the location, or may be separate from the carrier 3 and incorporated into the handling device 2. Other arrangements for detecting the presence/absence of holders will be appreciated by those of skill in the art and may be used as part of the detector 24. If the detector 24 is at least partially incorporated into the carriers 3, a communication device (e.g., electrical contacts, wireless communication devices, or other connection, etc.) may be provided so that the portion of the detector 24 in the carrier 3 can communicate holder presence/absence information to the handling device 2.

It will be similarly understood that the reader 22 may be partially or completely incorporated into carriers 3, e.g., by having laser scanners, wireless communication transceivers or antennas, electrical connections, etc. that communicate with individual holders 4. For example, if each holder 4 has an RFID device including identifier information, carriers 3 may have one or more antennas that communicate with the RFID devices (via a carrier-mounted antenna or transceiver) on each holder to determine the holder's identity and/or its location in the carrier 3. Alternately, each holder may have identifier information printed on it in conductive ink or other suitable substance, and electrical contacts on the carrier may contact the holder and detect identifier information, e.g., information encoded in a resistance pattern in the conductive ink or other substance. Other arrangements for detecting identifier information on holders 4 are possible and will be appreciated by those of skill in the art.

Operation of the handling device 2 may be as follows. In preparation for providing a plurality of sample holders 4 to a processing apparatus 1, an operator may place one or more carriers 3 on a handling device 2. (In the FIGS. 2-4 embodiment, one carrier 3 is positioned on the handling device 2.) The carrier reader 23 may then read the identifier information on the carrier 3 and store it and/or forward the information to the control system 10. Alternately, the reader 22 may read the identifier 31 on the carrier 3 if the carrier reader 23 is not provided. The operator may then pick up an individual holder 4, and position the holder 4 near the reader 22 so that identifier information is read from the holder 4. Suitable circuitry in the handling device 2 may store the identifier information and/or forward the information to the control system 10. The handling system 2 may provide an indication that the holder has been properly read, e.g., by displaying light pattern or alphanumeric text, emitting a tone, etc. Thereafter, the operator may place the holder 4 in a location in the carrier 3. (The operator may also remove a cap on the holder before placing it in the carrier or perform other operations as desired.)

To determine where the holder is placed in the carrier, the detector 24 may repeatedly look for any change in holder presence/absence at the carrier locations, e.g., by polling the photosensors to determine which sensor changes state during a time after the holder 4 identifier read. In this way, the handling device 2 may determine that the most recently read holder 4 has been placed in a particular location in the carrier 3. As a result, the operator may place the holder 4 in any location in the carrier 3 since the handling device 2 detects the location of the holder 4 automatically. Alternately, the handling device 2 may prompt the operator to place the most recently read holder 4 in a particular location in the carrier 3, e.g., by aurally or visually indicating a location in the carrier. If the operator places the holder 4 in the proper location, the handling device 2 may allow another holder to be read and placed in the carrier 3, and so on. If the holder 4 is placed in an incorrect location, the handling device 2 may prevent further reading of the holders 4 and placement in the carrier 3 until the holder 4 is placed in the proper location.

The handling device 2 and/or control system 10 may associate the holder location in the carrier 3 with the holder identifier information and/or the carrier identifier information, e.g., by storing the holder's identity/location/carrier information in a table, database or other suitable form. Identity/location/carrier information may alternately be stored in a memory associated with the carrier 3 so that subsequent processing apparatus can read the information directly from the carrier 3. However provided, the identity/location/carrier information may be provided to the processing apparatus 1 and used to correlate testing or other processing results with individual holders and/or used to determine what processes to perform for material withdrawn from sample holders.

Although in this illustrative embodiment sample holders are physically manipulated by an operator, it should be understood that the handling apparatus may include a robotic system or other automated device that moves sample holders and places them in carriers. Thus, the robotic system may manipulate holders so that the holders are read and then placed in a carrier. In such an arrangement, the holder reader 22 may be incorporated into the robot manipulator. Also, the detector 24 may take the form of circuitry in the robotic device that determines the location of the manipulator, and thus the holder 4, as the holder 4 is placed in the carrier, thereby indicating the location of the holder in the carrier. For example, position encoders in the robotic device may indicate the location of the sample holder, and thus indirectly indicate its location when placed in a carrier.

While the invention has been described with reference to various illustrative embodiments, the invention is not limited to the embodiments described. Thus, it is evident that many alternatives, modifications, and variations of the embodiments described will be apparent to those skilled in the art. Accordingly, embodiments of the invention as set forth herein are intended to be illustrative, not limiting. Various changes may be made without departing from the invention.

What is claimed is:

1. A sample handling apparatus for use with a processing apparatus that performs analytical processes on material in a plurality of sample holders, the sample handling apparatus comprising:
   a base constructed and arranged to support at least one carrier;
   a reading apparatus that inputs information representing a machine readable identifier on individual sample holders containing a material to be used in analytical processes, the reading apparatus being arranged to input information representing the machine readable identifier on an individual sample holder before the sample holder is placed in a carrier;
   at least one carrier, supported by the base, constructed and arranged to hold a plurality of individual sample holders at a plurality of unique locations, the at least one carrier including a machine readable identifier;
   a carrier reader secured to the base to read the machine readable identifier on the carrier while the carrier is supported by the base;
   a detector fixed relative to the base that detects the presence or absence of a sample holder at each location in a carrier supported by the base, wherein detection of the presence or absence of a sample holder is performed by the detector independently of reading a machine readable identifier on the sample holder; and
   a control system that receives a signal from the reading apparatus corresponding to an identifier read from an individual sample holder and receives a signal from the detector corresponding to a unique location in the carrier after the sample holder is placed in the carrier, and correlates the sample holder with the unique location in the carrier so that results from analytical processes performed on sample material removed from the sample holder can be correlated with the sample holder.

2. The apparatus of claim 1, wherein each sample holder has a unique barcode that is readable by the reading apparatus and uniquely identifies the sample holder.

3. The apparatus of claim 1, wherein the reading apparatus reads the machine readable identifier on each sample holder as an operator holds the sample holder.

4. The apparatus of claim 3, wherein the operator places each sample holder into a location in a carrier after the machine readable identifier is read by the reading apparatus.

5. The apparatus of claim 1, wherein the detector includes a plurality of photosensors that each correspond to a location in a carrier and detect the presence or absence of a sample holder in the corresponding location.

6. The apparatus of claim 1, wherein the control system provides information to the processing apparatus regarding an identity of each sample holder in each location of a carrier.

7. The apparatus of claim 1, wherein the at least one carrier includes a machine readable identifier that stores information regarding the identity of sample holders in each location of the carrier.

8. The apparatus of claim 1, in combination with a processing apparatus that performs at least one analytical process on material in sample holders.

9. The apparatus of claim 1, wherein the reading apparatus is adapted to read an identifier on at least one carrier into which sample holders are loaded.

10. The apparatus of claim 1, wherein the control system stores information regarding the identity of each sample holder, each sample holder's location in a corresponding carrier, and the corresponding carrier's identity.

11. The apparatus of claim 1, wherein the reading apparatus automatically reads the machine readable identifier on each sample holder.

12. A method for performing processes on material carried in sample holders, comprising:
   providing a plurality of sample holders, each sample holder carrying material;
   providing a carrier on a base;

reading an identifier on each of the sample holders before the sample holders are placed in the carrier on the base;

placing each of the sample holders in a corresponding location in a the carrier while the carrier is on the base;

detecting the presence of each of the sample holders at the corresponding location in the carrier independently of reading an identifier on each of the sample holders;

reading an identifier on the carrier while the carrier is on the base using a reader secured to the base;

storing information regarding the correlation of the identifier read from each sample holder, the corresponding location of the sample holder in the carrier, and the identifier read from the carrier; and providing the carrier and sample holders to a processing apparatus for performing analytical processes on the material in the sample holders.

13. The method of claim 12, wherein the step of providing a plurality of sample holders comprises providing a machine readable identifier on each sample holder.

14. The method of claim 12, wherein the step of reading an identifier comprises machine reading a machine readable identifier on each of the sample holders.

15. The method of claim 14, wherein the step of reading an identifier comprises having an operator manually move each sample holder near a reading apparatus that reads the identifier on each sample holder.

16. The method of claim 12, wherein the step of placing comprises manually placing each sample holder in a corresponding location in a carrier.

17. The method of claim 12, further comprising detecting the presence of each sample holder in its corresponding location in the carrier after the sample holder identifier has been read.

18. The method of claim 12, wherein the step of storing information comprises correlating an identifier read from a sample holder with a particular location in a carrier based on detecting the sample holder in carrier location that was previously unoccupied.

19. The method of claim 12, wherein the step of storing information regarding the correlation of the identifier read from each sample holder and the location of the sample holder in the carrier further comprises:

storing information regarding an identity of the carrier in which each sample holder is placed.

20. The method of claim 12, further comprising:

performing at least one analytical process on material in at least one of the sample holders;

obtaining results of the at least one analytical process; and correlating the results of the at least one analytical process with a specific sample holder.

21. A sample handling apparatus for use with a processing apparatus that performs analytical processes on material in a plurality of sample holders, the sample handling apparatus comprising:

a base constructed and arranged to support at least one carrier;

a reading apparatus that inputs information representing a machine readable identifier on individual sample holders containing a material to be used in analytical processes, the reading apparatus being arranged to input information representing the machine readable identifier on an individual sample holder before the sample holder is placed in a carrier;

at least one carrier, supported by the base constructed and arranged to hold a plurality of individual sample holders at a plurality of unique locations, the at least one carrier including a non-magnetic machine readable identifier;

a carrier reader to read the machine readable identifier on the carrier;

a detector fixed relative to the base that detects the presence or absence of a sample holder at each location in a carrier supported by the base, wherein the detection of the presence or absence of a sample holder is performed by the detector independently of reading a machine readable identifier on the sample holder; and a control system that receives a signal from the reading apparatus corresponding to an identifier read from an individual sample holder, and receives a signal from the detector corresponding to a unique location in the carrier after the sample holder is placed in the carrier, and correlates the sample holder with the unique location in the carrier so that results from analytical processes performed on sample material removed from the sample holder can be correlated with the sample holder.

* * * * *